(12) United States Patent
Pinto De Melo et al.

(10) Patent No.: US 8,932,485 B2
(45) Date of Patent: Jan. 13, 2015

(54) FLUORESCENT NANOPARTICLE COMPOSITES THEMSELVES, PROCESS FOR THE PREPARATION OF SUCH COMPOSITES, AND USE IN RAPID DIAGNOSIS SYSTEMS WITH AFFINITY TO BIOLOGICAL MOLECULES

(75) Inventors: Celso Pinto De Melo, Casa Forte (BR); César Augusto Souza De Andrade, Várzea (BR); Clécio Gomes Dos Santos, Engenho do Meio (BR)

(73) Assignee: Universidade Federal de Pernambuco-UFPE, Recife-pe (BR)

( * ) Notice: Subject to any disclaimer, the term of this patent is extended or adjusted under 35 U.S.C. 154(b) by 616 days.

(21) Appl. No.: 12/934,216

(22) PCT Filed: Mar. 23, 2009

(86) PCT No.: PCT/BR2009/000117
§ 371 (c)(1),
(2), (4) Date: Mar. 2, 2011

(87) PCT Pub. No.: WO2009/117798
PCT Pub. Date: Oct. 1, 2009

(65) Prior Publication Data
US 2012/0252002 A1    Oct. 4, 2012

(30) Foreign Application Priority Data
Mar. 24, 2008 (BR) ...................................... 0805991

(51) Int. Cl.
*C09K 11/06* (2006.01)
*A61B 5/055* (2006.01)
(Continued)

(52) U.S. Cl.
CPC ............ *G01N 33/582* (2013.01); *G01N 33/533* (2013.01); *G01N 33/587* (2013.01); *Y10S*
(Continued)

(58) Field of Classification Search
CPC ................................. G01N 33/553; B82Y 5/00
USPC .......... 252/301.33; 424/91.32; 435/6.1, 287.2; 436/501, 518, 525; 977/704, 773, 840, 977/902
See application file for complete search history.

(56) References Cited

U.S. PATENT DOCUMENTS

| 2005/0142567 A1 | 6/2005 | Su et al. |
| 2006/0175964 A1* | 8/2006 | Han et al. ...................... 313/506 |
| 2006/0263908 A1 | 11/2006 | Hirai |

FOREIGN PATENT DOCUMENTS

WO    WO 2006/061835 A1    6/2006

OTHER PUBLICATIONS

Alloisio et al, Photopolymerization of diacetylene-capped gold nanoparticles, 2008, Phys. Chem. Chem. Phys., 10, 2214-2220.*

(Continued)

*Primary Examiner* — Narayan Bhat
(74) *Attorney, Agent, or Firm* — Birch, Stewart, Kolasch & Birch, LLP

(57) ABSTRACT

The present invention provides fluorescent nanoparticle composites themselves, the process of preparing such composites, to systems for rapid diagnosis (as "kits") containing such composites, and to the use of such composites. In a preferential embodiment, the composites of the present invention have an affinity for biological molecules, such as DNA. The present invention also comprises the preparation of probes containing biological material, upon which are added fluorescent nanoparticle composites, making viable a rapid and economic biological diagnosis of, for example, diseases and genetic traits, notably in the medical and veterinarian fields. There is yet the fact that the absorption of radiation in the ultraviolet and visible regions, with the emission of light in the near ultraviolet and visible range, including in the colors of deep blue and/or green, provides advantageous use of its fluorescent properties in photovoltaic or electroluminescent devices, such as organic LEDs, or for the increase in luminous gain of fluorescent lamps, which represents another characteristic of the invention.

14 Claims, 5 Drawing Sheets

(51) Int. Cl.
*A21D 6/00* (2006.01)
*A23C 3/00* (2006.01)
*C12Q 1/68* (2006.01)
*C12M 1/34* (2006.01)
*G01N 33/58* (2006.01)
*G01N 33/533* (2006.01)

(52) U.S. Cl.
CPC .. 977/704 (2013.01); *Y10S 977/773* (2013.01); *Y10S 977/84* (2013.01); *Y10S 977/902* (2013.01)
USPC ............ 252/301.33; 424/9.32; 436/501; 436/523; 436/525; 435/6.1; 435/287.2; 977/704; 977/773; 977/840; 977/902

(56) References Cited

OTHER PUBLICATIONS

Grace et al, Organically dispersible gold and platinum nanoparticles using aromatic amines as phase transfer and reducing agent and their applications in electro-oxidation of glucose, 2007, Colloids and Surfaces A: Physicochem. Eng. Aspects, 302, 113-120.*

Periodic Table, Datasheet, Los Alomos National Laboratory, Downloaded from the internet [www.lanl.gov], printed on Jan. 3, 2013, p. 1.*

Kumar et al, Stabilized Gold Nanoparticles by Reduction Using 3,4-Ethylenedioxythiophene-polystyrenesulfonate in Aqueous Solutions: Nanocomposite Formation, Stability, and Application in Catalysis, Langmuir 2007, 23, 3401-3408.*

Yao et al, Grayscale Patterning of Polymer Thin Films with Nanometer Precision by Direct-Write Multiphoton Photolithography, Langmuir 2008, 24, 8939-8943.*

* cited by examiner

FLUORESCENT NANOPARTICLE COMPOSITES THEMSELVES, PROCESS FOR THE PREPARATION OF SUCH COMPOSITES, AND USE IN RAPID DIAGNOSIS SYSTEMS WITH AFFINITY TO BIOLOGICAL MOLECULES

FIELD OF THE INVENTION

The present invention refers to fluorescent nanoparticle composites. More specifically, it refers to the composites themselves, to the process of preparing such composites, to systems for rapid diagnosis (as "kits") containing such composites, and to the use of such composites. In particular, the composites of the present invention provide, among other advantages the absorption of radiation in the ultraviolet and visible regions, with the emission of light in the near ultraviolet and visible range, including in the colors of deep blue and/or green, providing advantageous use of its fluorescent properties in photovoltaic or electroluminescent devices, such as organic LEDs, or for the increase in luminous gain of fluorescent lamps. Besides that, the composites of the present invention have an affinity for biological molecules, such as DNA and RNA, also providing for applications in the medical and veterinarian fields, and in the diagnosis of genetic diseases as well as those caused by several pathogens.

BACKGROUND OF THE INVENTION

Molecular Diagnosis

The molecular diagnosis of diseases and genetic traits is an emerging field, particularly in the area of clinical analysis. Generally, it uses techniques from molecular biology for the study of DNA/RNA, of infectious agents, or of genetic changes in the organism itself, aiding in the diagnosis and prognosis of infectious and genetic diseases.

The more common molecular biology techniques currently used are: enzymatic amplification of the DNA (PCR), digestion of the genomic DNA strand or of PCR product with restriction enzymes, electrophoretic separation of the DNA or of the PCR product, hybridization of the DNA or PCR fragments with oligonucleotide probes, DHPLC and cytogenetic methods. These techniques allow the rapid genotyping of polymorphic markers, tracking of uncharacterized mutations. In particular, the cytogenetic methods, based on the microscopic observation of normal and abnormal chromosomes, allow the construction of cytogenetic maps of the genomes of many species. The FISH (fluorescent in situ hybridization) cytogenetic method is the most direct means of locating molecular and genetic markers in the cytogenetic map, allowing the integration between genetic and molecular markers. Probes are widely used for diagnosis, such as cosmid probes, which are unique sequences connected in small segments of certain chromosomes, being useful for the study of microdeletions. Other probes are used to detect translocations and highly repetitive sequences. However, one should point out that some of these techniques still have some limitations, such as false-positive signals, that can lead to an error in diagnosis.

A well-known molecular diagnosis system is the ELISA (Enzyme-Linked ImmunoSorbent Assay). This immune-enzymatic test allows the detection of specific antibodies in the serum of patients, being the first-line test in the diagnosis of HIV (human immunodeficiency virus) infection. The method for performing the test is based on the antibody-antigen interaction, with this test also being capable of detecting other substances, such as hormones.

The present invention refers to the fluorescent nanoparticle composites themselves, method for the preparation of these composites, system for rapid diagnosis (as "kits") containing such compounds, and functioning of said "kits". In particular, the composites of the present invention have specific characteristics regarding size and fluorescence, and have an affinity for biological molecules, such as DNA, RNA, and also proteins. The method for the preparation of these compounds is also described in the present invention. Plus, the present invention describes the method of preparation for an adequate probe (named here as "support") containing biological material of the organism one wishes to study. Upon this support the fluorescent nanoparticle composites and the patient's biological material are added, comprising a diagnostic system, designated here as the ELINOR (from "Enhanced Luminescence from Inorganic/Organic nanocomposites") test, for the diagnosis of diseases caused by several pathogens and/or genetic diseases, amongst other things. The present invention has application mainly in the medical and veterinarian fields.

The patent literature describes an ample variety of probes for the diagnosis of specific diseases. However, most of the documents deal with methods that use the PCR molecular biology technique, requiring the amplification of the biological molecule that one wishes to study in order to perform the diagnosis. One can exemplify the methods for the diagnosis of diseases by the documents presented below.

Document U.S. Pat. No. 6,258,570 deals with a method for the diagnosis of viral meningitis using PCR, as does document U.S. Pat. No. 7,041,255, which uses the same technique to detect infection by the dengue virus. Likewise, the PCR is used for the diagnosis of the human papilloma virus (HPV), as described by document U.S. Pat. No. 6,027,89, and of *Streptococcus pneumoniae*, as described by U.S. Pat. No. 6,869,767.

The present invention differs from all of those documents by not requiring a step of amplification (such as the one performed in the PCR technique) in order to perform the molecular diagnosis.

The patent literature also reveals several examples of fluorescent biosensors containing gold, out of which we highlight the most relevant.

Document US 2007/0059693 describes a biosensor containing a fluorescent surface, molecules of nucleic acid, and a fluophore. The fluorescent surface may be a metal, including gold. The molecules of nucleic acid must have one of the ends bound to the fluorescent surface and the other end to a fluophore. This molecule of nucleic acid may also have internal hybridization regions that, when hybridized, form a "staple". In these cases, the fluophore will be close to the fluorescent surface, allowing fluorescence to occur. The present invention differs from that document due to the support surface not being necessarily fluorescent nor metallic, and not requiring that the molecules of nucleic acid form a "staple" in order to emit fluorescence.

Document US 2005/0196876 describes a method for the analysis of the content of a biological sample through the contact of the sample with a nanoporous biosensor. This biosensor contains probes that bind to the samples forming complexes that will be bound to a second probe. That probe will be illuminated so as to send a specific fluorescent signal. In an optional configuration, this biosensor may have a layer of gold. The present invention differs from the aforementioned document by dealing with fluorescent nanoparticles containing gold, there being no need to bind to more than one probe.

Document U.S. Pat. No. 6,773,884 describes a method for the detection of nucleic acids in which those molecules are put in contact with one or more nanoparticles of gold bound to oligonucleotides and to fluorescent molecules. When the hybridization occurs, the interaction of these molecules with the oligonucleotides suffers an alteration detectable as changes in the florescence. The present invention differs from the aforementioned document by dealing with nanoparticles in which the gold is covered by polymers, and by being deposited over the biological molecules studied, there being no need for the presence of oligonucleotides bound to the nanoparticle.

Document U.S. Pat. No. 7,083,928 describes the detection of negatively charged polymers using water-soluble cationic polythiophenes. The negatively charged polymers include biological molecules such as nucleic acid. This polymer may be bound to a conductive support, such as a gold surface. When the polymer is detected, there is a change in the electronic load, fluorescence, or color, The present invention differs from the aforementioned document by dealing with nanoparticles of gold covered by polymers that interact with the biological molecules, with the gold not being part of the adequate support that will immobilize the biological molecules.

Therefore, no document was found describing, nor suggesting, the fluorescent nanoparticle composites themselves, their form of preparation, the systems containing such composites for use in diagnostic "kits", or form of functioning for such systems.

SUMMARY OF THE INVENTION

It is one of the objects of the present invention the production of fluorescent composites of nanoparticles on themselves, comprising:
a) at least one oxidizing agent;
b) at least one stabilizer agent;
c) at least one monomer.

In a preferential realization, the oxidizing agent is $HAuCl_4$.

In a preferential realization, the stabilizer agent is (3-mercaptopropyl)trimethoxy silane (MPS).

In a preferential realization, the monomer is aniline.

In a preferential realization, the fluorescent composites are composed by conducting polymer chains enveloping metallic nanoparticles with linear sizes of 5 nm or less.

In a preferential realization, the properties of the composites are changed by variation of their oxidation state and/or change of the pH of the medium.

It is an additional object of the present invention to provide a process for the preparation of composites of fluorescent nanoparticles involving the addition, under mechanical agitation, at least one oxidizing agent, at least one stabilizer agent, and at least one monomer to at least one alcohol or a polar solvent.

In a preferential realization, the above referred mechanical agitation occurs between 600 and 1,200 rpm.

It should be understood that the adjustment of the oxidizing agent oxidation state and/or pH provides the adjustment of the properties of said composites and that the monomer choice determines the composite affinity to biological molecules with negative or positive superficial charge.

It is an additional object of the present invention, one system for rapid diagnosis comprising:
a) at least one fluorescent composite;
b) at least one short nucleotide sequence;
c) an appropriate substrate for the immobilization of the referred sequence;
d) genetic sample of the patient;

In a preferential realization, the referred sequence of nucleotides is part of a single stranded DNA.

In a preferential realization, the referred substrate is a glass slide.

In a preferential realization, the referred immobilization is performed by the deposition of approximately 1 µL of a 100 pmol solution of biological material on the substrate.

In a preferential realization, the genetic material of the patient is the "total DNA", obtained after a simple DNA extraction from a sample of material provided by the patient.

It is an additional object of the present invention to provide an improved process for diagnosis of genetic and/or infectious diseases. In an preferential realization, the process of diagnosis of the invention comprises:

a) to immobilize a short single strand of the nucleotide sequence that uniquely characterizes the organism to be investigated disposed on a to least one appropriate support;

b) to establish physical contact among the immobilized material of a), the genetic material obtained from the patient and the composite of fluorescent particles;

c) to determine the corresponding fluorescence emission signal.

In preferential realization, the genetic material of c) is the "total DNA", obtained after a simple extraction of the DNA.

It is yet another object of the present invention to provide the use of the fluorescent composites of the invention for the preparation of photovoltaic devices, such as solar cells, electroluminescent devices, such as organic LEDs, sensors, or for the increase in the lighting efficiency of fluorescent lamps.

It is yet another object, the present invention provides the use of the composites of the invention for the preparation of reagents and/or consumable items, such as, but not limited to, fluorescent markers, for use in diagnosis.

In a preferential realization, the intensity of the fluorescence emission indicates the presence or absence of the biological material of the organism to be examined in the genetic sample obtained from the patient.

In an alternative preferential realization, the composite is combined to magnetic composites, in such manner to allow the use of external magnetic fields to assure the increase and/or separation of the fluorescent fraction that contains the biological material of interest.

In another preferential realization, the composite is prepared by use of functionalized polymers, i.e., polymers that are bound in a covalent manner to the short nucleotide sequence, so that the fluorescent tagging of the genetic material (including native and unfolded protein) of the patient can occur still in solution phase, with no additional need of its anchorage on a solid substrate.

These and objects of the present invention will be better understood and properly appreciated after analysis of the detailed description of the invention and the corresponding accompanying claims.

DETAILED DESCRIPTION OF THE INVENTION

Figure 1:
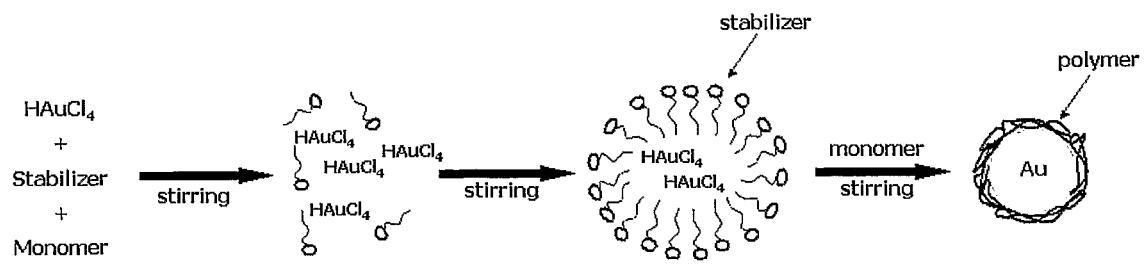
FIG. 1 is a schematic representation of the preparation route to obtain the fluorescent composites ((Au nanoparticles)/(conducting polymer)).

The composites of the invention are useful for different applications, including: the preparation of photovoltaic devices, such as solar cells, and electroluminescent devices, as organic LEDs, leading in both cases to a substantial increase in their quantum efficiency; the increase in the lighting efficiency of fluorescent lamps; the preparation of reagents and consumable items for diagnosis procedures, amongst other applications. The composites of the present invention provide, among other advantages, the absorption of incident light in the ultraviolet or visible regions and the emission of light in the ultraviolet and visible region, inclusive in the "deep blue" and/or green colors, providing a special advantage in their use in photovoltaic devices, such as solar cells, or in electroluminescent devices, as organic LEDs, or for the increase in the quantum yield of lighting systems, such as fluorescent lamps. In regard to the latter application, the composites of the present invention provide a environmentally friendlier and more energy efficient alternative to the phosphors presently used in the internal layer of coverage of fluorescent lamps to assure the ultraviolet quantum cut-off and that are a source of pollution when not properly discarded. The composites of the invention can be prepared so as to provide emission in different colors and with wide-range adjusting intensities, according to the tuning of their composition and preparation manner.

The composites of the present invention have affinity for biological molecules, such as DNA, RNA, or proteins, providing also applications in the areas of human and animal health and in the diagnosis tests for diseases caused by different pathogenic agents. In this regard, the following examples do not have the purpose of limiting the range of the invention, but rather only illustrate one of the innumerable manners of realizing the invention.

It is understood by "biological material" the group of compounds that comprises, but it is not limited to, DNAs, RNAs, proteins, lipids, peptides, non-codifying RNAs, and/or any other biological material that could be represented by a single chain or single strand.

It is understood by "genetic material of the patient" the group of biological material that comprises, but it is not limited to, the biological material of any organism that could be present in a small amount of blood or obtained from a simple collection of epithelial or mucosa cells, and/or from secretions and/or excretions of the patient. It is understood by "oxidizing agent" is a salt in which the cation is selected from the group comprising metals chosen from groups 1B to 8B of the periodic table. This group of compounds comprises, but it is not limited to, to gold compounds, such as $HAuCl_4$. Preferentially, the gold atom is in the 3+ oxidation state. However, other salts of metals of the 1B to 8B families can be used, provided that their oxi-reduction potential allows the oxidation of the monomer, leading to the formation of the polymer. The present inventors have prepared other compounds not only based on Au, but also on Ag and Cu, and using other monomers besides pyrrole, such as derivatives of aniline and thiophene. In a similar way, the experts in the field will understand that metals such as nickel, platinum and palladium can also be used. The present inventors have also prepared other composites in which the conducting polymer was used in the presence of metallic oxides, in such manner as to obtain composites that exhibit at the same time properties of fluorescence and magnetism. It is understood by metallic oxides, compounds, the general class of compounds containing oxygen and metals, such as, but not limited to, iron and titanium.

It is understood by "monomer" any compound that can be polymerized by the oxidizing agent. Namely, it is chosen from the group that comprises, but it is not limited to, the smallest repetitive unit of a polymer, as those derived from aniline ($C_6H_5NH_2$), thiophene ($C_4H_4S$), pyrrole ($C_4H_5N$), or precursor molecules of the respective polymers, polyaniline, PEDOT ((poly(3,4-ethylenedioxythiophene)poly(styrene-sulfonate)), PTAA (polythiophene acetic acid) and polypyrrole, and/or a mixture or blend of them.

It is understood by "stabilizing agent", the group of compounds that comprises, but it is not limited to, silanes, such as (3-mercaptopropyl)trimethoxy silane (MPS), (3-mercaptopropyl)methyldimethoxysilane, (3-mercaptopropyl)triethoxysilane e (3-mercaptoethyl)trimethoxysilane and/or a mixture of them.

It is understood by "alcohol" the group that comprises, but it is not limited to methanol, ethanol, propanol, butanol, glycerol, ethylene glucol and/or a mixture of them.

Example 1

Synthesis and Characterization of the Nanoparticles

Example 1.1

Preparation of the Nanoparticles

The preparation of nanoparticles was performed (see scheme in FIG. 1) in a round bottom glass flask containing ethanol (20 mL) and the compounds: aniline (Ani-$C_6H_5NH_2$) (0.030 mol/L), 3-mercaptopropyl-trimethoxy-silane (MPS-$C_6H_{16}O_6SSi$) ($6.46 \times 10^{-2}$ mol/L) and $HAuCl_4 \cdot xH_2O$ (0.81 mmol/L), which were subsequently added and subject to energetic agitation (1,100 rpm). Aniline (Ani-$C_6H_5NH_2$) was acquired from VETEC (Brazil) and only used after distillation in a Kugelrohr apparatus. The other compounds were bought from Aldrich Co. (USA), and had at least 99% degree of purity. All subsequent experiments were performed in the 48 hours time interval after the mixtures.

Example 1.2

Characterization of the Nanoparticles

Photoluminescence properties were measured by use of a quartz cuvette (1 cm and 5 mL) in a PC1 (ISS, USA) spectrofluorimeter at $(20\pm1)°$ C. The samples were monitored at different pH values by use of two luminescence matrices: (1)

in the 200 to 360 nm excitation range and emission in the 370 to 600 nm interval; and (2) in the 270 to 330 nm excitation range and emission in the 280 to 600 nm interval. Morphological analyses were performed by scanning electron microscopy (SEM), by use of a JSM-5900 (JEOL, Japan) electron microscope. The samples were placed atop a glass substrate and fixed by a carbon tape. After this, the samples were covered by a thin gold layer by use of a sputtering (BalTec SCD 050). The size of the particles was determined by a light-scattering method by use of a Zetasizer Nano-ZS90 instrument (Malvern).

Example 2

Characteristics of the Nanoparticles

Figure 2:
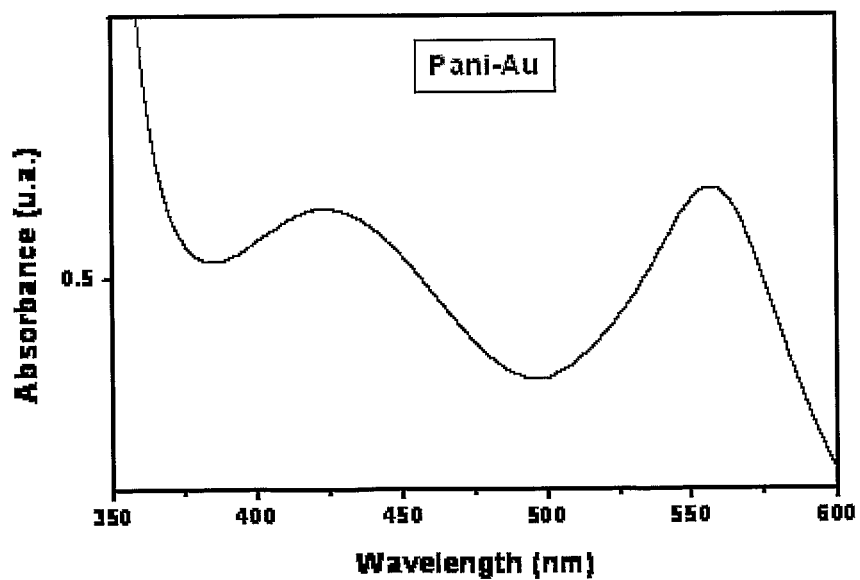
FIG. 2 is the UV-Visible absorption spectrum of the Au/PANi composites, where the plasmon band (associated to the reduced gold forming metallic nanoparticles) and the polaron band (associated to the monomer oxidation process leading to the formation of the polymer).

Gold nanoparticles with diameters of the order of ~5 nm exhibit in their absorption spectrum a surface plasmon (SP) band centered in 525 nm. The UV-Vis spectrum of the composites is shown in FIG. 2, where once can observe the strong presence of a SP band at 560 nm. It is known that the wavelength and the intensity of the SP band vary according to the size, shape and the "interparticle" dielectric medium, and that it is also sensitive to the relative molar fraction (stabilizing agent)/Au [J. Am. Chem. Soc. 2003, 125, 9906]. It is also known that polyaniline (PANi) exhibit two characteristic absorption bands (324 nm and 625 nm) in the UV-Vis region.

In the method used in the present invention, the gold containing compound ($HAuCl_4.xH_2O$) acts as an oxidizing agent, i.e., the trigger of the aniline polymerization, while a mercapthosilane is included as a co-stabilizer of the formed metallic nanoparticles. In the fluorescence matrix of the PANi-Au sample, one can verify that the composite exhibit luminescent properties in the visible region, since the composite presents a peak of photoluminewscence centered close to 400 nm when excited in the ultraviolet (350 nm) region. The use of gold nanoparticles and conducting polymers in light emitting diodes, while trying to increase the electroluminescence stability and quantum yield, was discussed in a recent paper [Chem. Mater.: 2004, 16, 688-692], where it is proposed that the reason for the observed effects are the increased roughness of the metallic cathode surface and the improvement of the balance of the injected charges promoted by the metallic nanoparticles. On the other hand, examples of water soluble and highly luminescent nanoparticles were recently published [Physical Review Letters vol. 93(7) 2004, pp. 77402-1 77402-4], where the intense luminescence was attributed to the formation of metallic aggregates that would lead to the injection and transport of charge through the discrete levels of energy. Differently from the above related examples, in the present case the method used has allowed the inventors to prepare gold nanoparticles with sizes of the order of 5 nm (or less), enveloped by a "shell" of conducting polymers, whose dielectric properties can be changed by varying either their oxidation state and/or the pH of the medium where they are dispersed. In this manner, at least in principle one can tune the emission wavelength of the composite by properly adjusting the dielectric properties of the medium. Measurements of the quantum yield of the first samples of the composites have indicated values in the 1.5 to 7.5% interval; however, modifications in the method of preparation already implemented have allowed the inventors to increase the quantum yield, as well as emission of the same system in different wavelengths.

Figure 3:
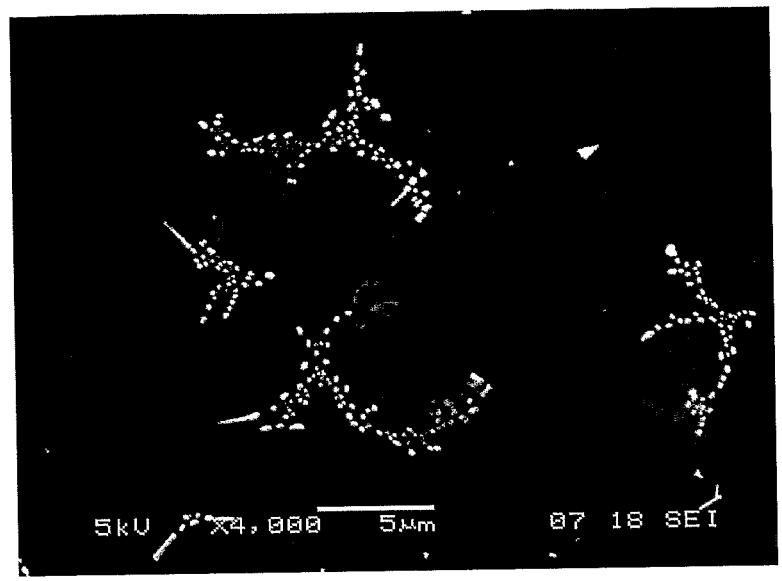
FIG. 3 is a scanning electron microscope image of the fluorescent composites (Au nanoparticles)/(conducting polymer). (Magnifying factor of 4,000×).
Figure 4:
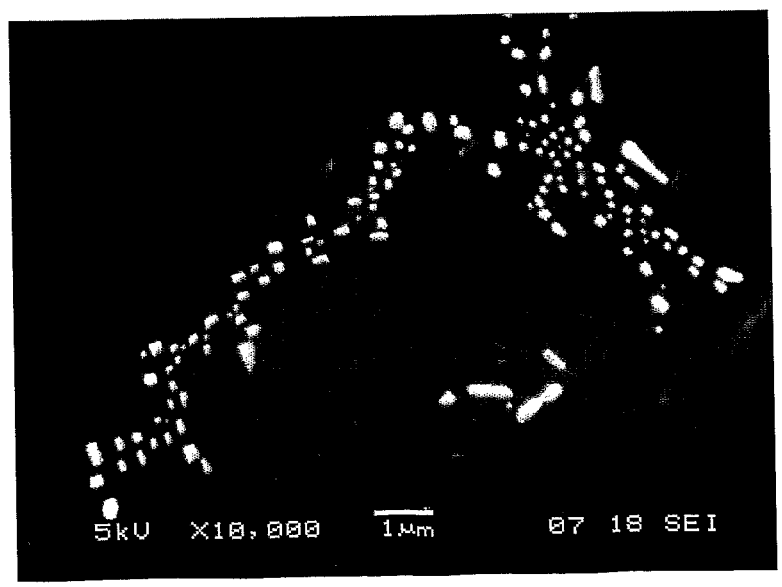
FIG. 4 is a scanning electron microscope image of the fluorescent composites (Au nanoparticles)/(conducting polymer). (Magnifying factor of 10,000×).

Scanning electron microscopy (SEM) shows that the nanoparticles tend to align themselves in more complex structures (FIGS. 3 and 4).

Figure 5:
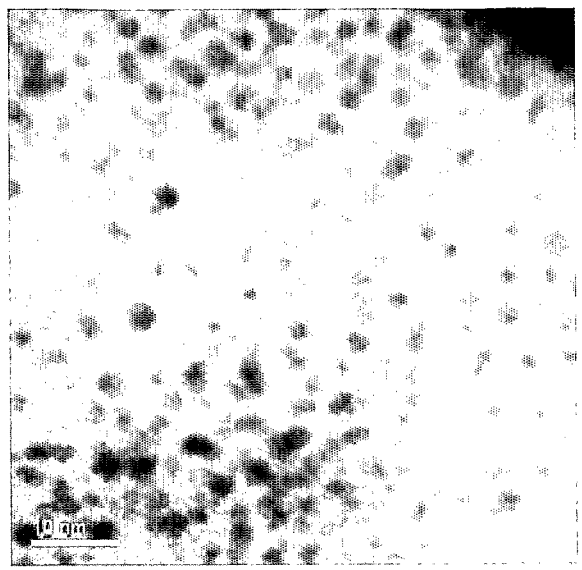
FIG. 5 is a transmission electron microscope image of the fluorescent composites (Au nanoparticles)/(conducting polymer).
Figure 6:
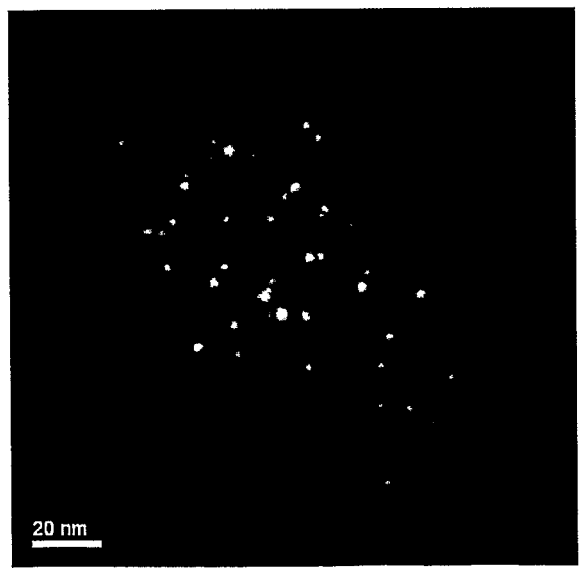
FIG. 6 is a transmission electron microscope image in dark field of the fluorescent composites (Au nanoparticles)/(conducting polymer). The lighter regions indicate the presence of metallic nanoaggregates enveloped by the polymeric chains.

Transmission electron microscopy (TEM) images in bright field were obtained for the composites object of the present invention (FIG. 5), where one can identify the presence of agglomerates with an average diameter of 50 nm. In addition, in the dark field mode, one can clearly see a regular and homogeneous distribution of gold nanoparticles (FIG. 6). It is important to stress that in light scattering experiments the average size of the agglomerates of the composites was estimated to be in the 150 to 300 nm range.

Figure 7:
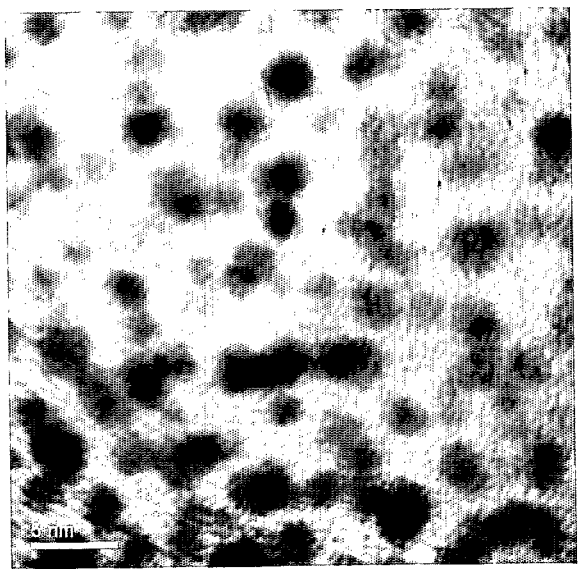
FIG. 7 is a transmission electron microscope image of the fluorescent composites (Au nanoparticles)/(conducting polymer) where the metallic nanoaggregates can be seen.
Figure 8:
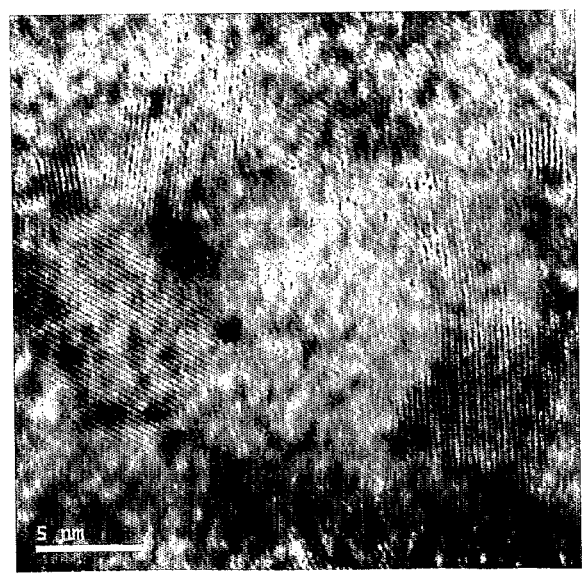
FIG. 8 is a high-resolution transmission electron microscope image of the fluorescent composites (Au nanoparticles)/(conducting polymer).
Figure 9:
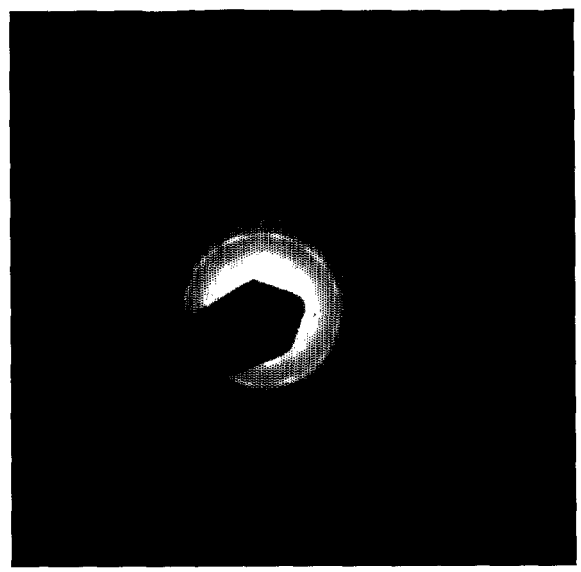
FIG. 9 is a X-ray diffraction image of the fluorescent composites (Au nanoparticles)/(conducting polymer).

FIG. 7 reveals that there is a monodisperse distribution of nanoparticles of sizes varying from 2 to 5 nm, even though in some cases formation of geminal particles—a well-known characteristic of gold nanoparticles—could be identified. A High Resolution Transmission Electron Microscopy (HR-TEM) image of the hybrid gold/(conducting polymer) nanocomposite reveals the presence of crystalline structures (FIG. 8), an observation that is confirmed by examining the corresponding X-ray diffraction (XRD) pattern (FIG. 9).

Example 3

Diagnosis Kits Containing the Fluorescent Nanostructured Composites

Due to the fact that it is possible to adapt the methodology proposed in the present invention to large scale production with low capital investment and at a very price per unit, the associated technology has its low cost and speed of implementation as principal comparative advantages over the methods usually adopted in the diagnosis of infectious diseases caused by bacteria or virus, factors that accompanied by a greater generality and flexibility of application. One can identify some important characteristics of the use of the fluorescent nanocomposites in diagnosis kits:

(1) the specificity towards the presence of a given pathogenic agent is determined by the nature of the fragment of the biological material (such as a DNA single strand) immobilized in the probe, so that the technique do not is limited on that regard, and can be used for the identification of any organism for which a specific short sequence of biological material, such as DNA, can be obtained;

(2) the technology is of general use for the diagnosis of any disease:
   whose origin can be: a) attributed to a known pathogenic agent, or b) associated to the presence of a specific sequence of biological material (such as DNA or RNA), even if human (and so it opens the possibility of using the technology for the investigation not only of diseases already installed but also for the analysis of genetic tendency of patients with regard to the future development of hereditary pathologies;

(3) the amount of biological material to be used in the diagnosis assays is extremely small (e.g., a volume of 1 μL of a 100 pmol solution of biological material, such as DNA);

(4) the preparation of the probes containing the sequence of the biological materials (such as DNA) is a step that can be adapted to large scale production, once again at a very low cost;

(5) the manipulation of the genetic material obtained from the patient to use in the proposed diagnosis procedure do not require steps related to separation and amplification of the DNA of interest, via polymerase chain reaction (PCR) and similar techniques;

(6) the result of the diagnosis assay has a conclusive character (i.e., positive/negative) and it can be obtained in a matter of minutes, with no need of using any kind of culture medium;

(7) the result of the diagnosis assay is based in the observation of the intensity of the fluorescence signal, indicating the presence or absence of the nucleotide sequence of interest;

(8) in the case of existence of genetic variation of the pathogenic agent in different subtypes (as in the case of the dengue virus, for example), the assay probe can be prepared in such manner as to contain biological material of each subtype to be investigated, and hence a single test can provide a conclusive answer with regard to the presence of any variety of the pathogen in the genetic sample provided by the patient;

(8) in the case in which the symptoms exhibited by the patient can be attributed to a limited number of possible pathogenic agents (as, for example, in the case of hospital acquired infections, or in the case of victims of accidents with deep perforations and wounds), the probe can be prepared in such manner as to contain biological materials (nucleotide sequence) of each one of the agents, so that in a single and rapid exam the diagnosis can be conclusive for the presence of any of them;

Since this technology can be applied to the diagnosis of the presence of any pathogenic agent, one can choose the nature of the microorganism to be investigated in appropriated tests, defined from the problems of possible interest for the public health of a given country or region. The rapid diagnosis kit here proposed can be used, but is not limited, to the diagnosis of: dengue virus: ii) tuberculosis; iii) hepatitis C; iv) human papillomavirus (HPV), v) leishmaniasis, vi) rapid identification (from within a pre-selected range of options) of the cause of hospital acquired infections; vii) rapid identification of meningococcus infections; viii) bioterrorism hazards, besides ix) genetic screening of hereditary diseases (such as Tay-Sachs, phenilketonuria, breast cancer, among others). A few examples are discussed below.

Example 3.1

Diagnosis of the Presence of the Human Papillomavirus, HPV

The diagnosis procedure uses a short sequence of a single nucleotide strand consisting of 20 bases of the variety 16 of HPV. The quality of the response can be attested when a negative answer was obtained whenever the probe was exposed to a double strand of the variety 18 of HPV with circa of 500 base pairs and a positive answer only when the probe was exposed to double strand with 500 bases pairs of the variety 16 of HPV.

Example 3.2

Diagnosis of the Presence of the Dengue Virus

The diagnosis procedure uses a short single strand consisting of 22 bases of the subtype 2 of the dengue virus. The quality of the response is associated to a negative answer when the probe was exposed to a double strand non-complementary to the original sequence used and to a positive diagnosis when the probe was exposed to a double strand containing 22 base pairs of the subtype 2 of the virus dengue.

Example 3.3

Diagnosis of the Presence of the Human Papillomavirus (HPV) and the Sensitiveness of the Response to the Presence of Alleles The diagnosis procedure uses short single strand sequences of 19 (MBL54mt) and 22 (MBL57mt) bases corresponding to human lectin responses to different HPV varieties, some of them containing mutations in specific positions that could block the hybridization of the DNA chains of the pathogenic agent present in the material of the patient. The type of response (positive or negative answer) obtained, respectively, for homozygous and heterozygous patients define the sensitiveness of the technology as excellent.

In all of the examples above referred, a short sequence of a single strand of nucleotide chain (DNA or RNA) was anchored atop a previously silanized glass substrate, and afterwards a small drop of the mixture (composite (metal nanoparticle)/(conducting polymer)+(total DNA of the patient)) was added. The system was subsequently washed with running distilled water and, after waiting for about three minutes for drying, the substrate was placed in a fluorescence microscope for analysis. In case of existence of genetic material of the pathogenic agent in the biological material obtained from the patient (the "total DNA"), a long nucleotide strand of the pathogenic agent will hybridize to the immobilized short sequence, and retain a larger amount of fluorescent composite: a "positive" answer will then arise. If the hybridization did not occur, only a smaller amount of the composite Will remain attached to the short immobilized sequence of nucleotide, and as a consequence the fluorescence signal will be minimum (basal): the "negative" answer. It has to be noted that in a series of tests with the HPV, one of the 20 bases was deliberately altered, changing an original "positive" answer to "negative"; hence, the sensitiveness of the here proposed procedure is able to discriminate the change of a single base in 20.

Yet other applications of the composites object of the present invention can be immediately apprehended by the experts in the field, once they have been exposed to the present information. Among others, one can call attention to the rapid in situ diagnosis in situations such as: diagnosis of diseases in the battlefield; rapid identification of anthrax and other forms of bioterrorism contamination; biological contamination of food and beverage products in general, as in the case of control of quality of grains and cereals; biological assays in the field for in situ identification and comparative analysis of specimens with regard to pre-selected biological characteristics (screening in the field or biobarcoding), eliminating the need of collecting and transporting redundant material; and methods of forensic identification. In regard to the last subject, the composites of the present invention can act as "nanoluminol"; a fairly recent publication of the University of San Diego shows that DNA portable detectors may offer substantial advantages over the present technology. Even tough the technology adopted in such reference is much more complex and expensive (ion-selective field-effect transistor—ISFET) than that discussed in the present invention, it is an important example of the actual need of new developments this area of expertise.

The skilled in the art will immediately recognize the value of the present teachings and they also will understand that variations in the forms of executing the invention herein exemplified must be considered as within the spirit of the present invention and in the general scope of the accompanying claims.

The invention claimed is:

1. A process for preparing fluorescent nanoparticle composites which consists essentially of polymerizing, under mechanical agitation, at least one monomer, in the presence of a salt of metallic nanoparticles as an oxidizing agent, at least one stabilizer, and an alcohol or a polar solvent,
   wherein the fluorescent nanoparticle composites are fluorescent emitting in the visible wavelength region, wherein the fluorescent nanoparticle composites are 5 nm or less, and wherein the mechanical agitation is conducted between 600 and 1200 rpm.

2. The process, according to claim 1, wherein the oxidizing agent is a salt in which the cation is selected from the group consisting of metals chosen from groups 1B to 8B of the Periodic Table.

3. The process, according to claim 1, wherein the oxidizing agent is $HAuCl_4$.

4. The process, according to claim 1, wherein the stabilizer agent is a compound comprising a mercapto and/or silane group.

5. The process, according to claim 1, wherein the stabilizer is 3-mercaptopropyl-trimethoxy-silane.

6. The process, according to claim 1, wherein the monomer is aniline.

7. The process, according to claim 1, wherein the alcohol is ethanol.

8. A process for preparing fluorescent nanoparticle composites capable of identifying DNA chains which comprises polymerizing, with mixing, a monomer selected from the group consisting of aniline, thiophene, pyrrole, 3,4-ethylenedioxythiophene, styrene sulfonate, thiophene acetic acid and mixtures thereof, in a medium containing an oxidizing agent of metallic nanoparticles of a salt in which the metallic cation is selected from Groups 1B to 8B of the Periodic Table, a stabilizing agent, and an alcohol or a polar solvent, wherein the fluorescent nanoparticle composites thus formed comprise fluorescent metallic nanoparticles enveloped by a shell of the conducting polymers, wherein the fluorescent nanoparticle composites are fluorescent emitting in the visible wavelength region, and wherein the fluorescent nanoparticle composites are 5 nm or less.

9. The process of claim 8, wherein the metallic nanoparticles have dielectric properties which can be changed by varying the oxidation state or the pH of the medium in which they are dispersed.

10. The process of claim 9, wherein the metallic nanoparticles have a size of 5 nm or less.

11. The process of claim 8, wherein the oxidizing agent is a metal salt of a metal selected from the group consisting of titanium, nickel, palladium, platinum, copper, silver and gold.

12. The process of claim 8, wherein the alcohol is selected from the group consisting of methanol, ethanol, propanol butanol, glycerol, ethylene glycol and mixtures thereof.

13. The process of claim 8, wherein the stabilizer is selected from the group consisting of (3-mercaptopropyl) trimethoxy silane, (3-mercaptopropyl) methyldimethoxysilane, (3-mercaptopropyl)triethoxysilane and (3-mercaptoethyl)triethoxysilane.

14. The process of claim 8, wherein the mixing is conducted with agitation at 600-1200 RPM.

* * * * *